(12) United States Patent
Mu

(10) Patent No.: US 10,004,456 B2
(45) Date of Patent: Jun. 26, 2018

(54) INTELLIGENT DENTAL ORNAMENT AND METHOD OF USING THE SAME

(71) Applicants: BOE TECHNOLOGY GROUP CO., LTD., Beijing (CN); BOE OPTICAL SCIENCE AND TECHNOLOGY CO., LTD., Suzhou (CN)

(72) Inventor: Zongmei Mu, Beijing (CN)

(73) Assignees: BOE TECHNOLOGY GROUP CO., LTD., Beijing (CN); BOE OPTICAL SCIENCE AND TECHNOLOGY CO., LTD., Suzhou, Jiangsu (CN)

( * ) Notice: Subject to any disclaimer, the term of this patent is extended or adjusted under 35 U.S.C. 154(b) by 39 days.

(21) Appl. No.: 15/327,351

(22) PCT Filed: Feb. 18, 2016

(86) PCT No.: PCT/CN2016/074014
§ 371 (c)(1),
(2) Date: Jan. 18, 2017

(87) PCT Pub. No.: WO2017/054396
PCT Pub. Date: Apr. 6, 2017

(65) Prior Publication Data
US 2017/0303852 A1 Oct. 26, 2017

(30) Foreign Application Priority Data
Sep. 29, 2015 (CN) .......................... 2015 1 0631896

(51) Int. Cl.
*A61B 5/00* (2006.01)
*A61B 5/07* (2006.01)
*A61B 5/145* (2006.01)

(52) U.S. Cl.
CPC .............. *A61B 5/682* (2013.01); *A61B 5/076* (2013.01); *A61B 5/14503* (2013.01);
(Continued)

(58) Field of Classification Search
CPC .............. A61B 5/1455; A61B 5/14551; A61B 5/14532; A61B 5/1459; A61B 5/1495;
(Continued)

(56) References Cited

U.S. PATENT DOCUMENTS 4,629,424 A 12/1986 Lauks et al.
6,058,321 A * 5/2000 Swayze ................ A61B 5/0448
600/310
(Continued)

FOREIGN PATENT DOCUMENTS

CN 101360463 A 2/2006
CN 1997421 A 7/2007
(Continued)

OTHER PUBLICATIONS

Chinese Office Action with English language translation, dated Jul. 22, 2016, Chinese Application No. 201510631896.8.
(Continued)

*Primary Examiner* — Eric Winakur
*Assistant Examiner* — Chu Chuan (J J) Liu
(74) *Attorney, Agent, or Firm* — Womble Bond Dickinson (US) LLP

(57) ABSTRACT

The invention provides an intelligent dental ornament and a method of using the same, the intelligent dental ornament comprising: a dental ornament body with a cavity, a tester located within the cavity and for detecting a physiological parameter, a battery used by the tester, and a trigger switch for triggering the tester to start test; the dental ornament body is further provided with a through-hole for at least one pipette of the tester stretching out of the dental ornament body, and a sealing cover for sealing the through-hole. When the trigger switch activates the tester, the sealing cover is opened, and the pipette of the tester stretches out of the dental ornament body through the through-hole to obtain the (Continued)

saliva of the subject, and the physiology parameter in the saliva is detected, and the detection result is sent to an external device in communication with the tester. The intelligent dental ornament can intelligently detect the physiology parameters such as the blood glucose or alcohol content without affecting the aesthetics of the dental ornament, and has the advantages of simple operation, reducing pain of the user, being reusable, and reducing cost.

20 Claims, 4 Drawing Sheets

(52) U.S. Cl.
CPC ...... *A61B 5/14507* (2013.01); *A61B 5/14532* (2013.01); *A61B 5/4845* (2013.01); *A61B 2560/0214* (2013.01)

(58) Field of Classification Search
CPC ... A61B 5/682; A61B 5/4845; A61B 5/14507; A61B 5/14503; A61B 5/076; A61B 5/72
See application file for complete search history.

(56) References Cited

U.S. PATENT DOCUMENTS

| | | | | |
|---|---|---|---|---|
| 8,742,623 B1* | 6/2014 | Biederman | .......... | A61B 5/6821 307/80 |
| 2004/0158194 A1* | 8/2004 | Wolff | .................. | A61C 19/063 604/66 |
| 2006/0116561 A1* | 6/2006 | Tricca | .................... | A61B 5/682 600/309 |
| 2007/0106138 A1* | 5/2007 | Beiski | .................... | A61B 5/682 600/349 |
| 2009/0210032 A1* | 8/2009 | Beiski | .................. | A61N 1/0548 607/59 |
| 2014/0275857 A1* | 9/2014 | Toth | ........................ | A61B 5/682 600/301 |
| 2015/0216641 A1 | 8/2015 | Popa-Simil et al. | | |

FOREIGN PATENT DOCUMENTS

| | | | |
|---|---|---|---|
| CN | 103499621 | A | 1/2014 |
| CN | 104768457 | A | 7/2015 |
| CN | 104921833 | A | 9/2015 |
| CN | 105125310 | A | 12/2015 |
| CN | 205054488 | U | 3/2016 |
| JP | 2004167120 | A | 6/2004 |
| WO | WO-9701992 | A1 | 1/1997 |
| WO | WO-2005115225 | A2 | 12/2005 |
| WO | WO-2013049327 | A2 | 4/2013 |
| WO | WO-2015112638 | A1 | 7/2015 |

OTHER PUBLICATIONS

International Search Report with English language translation, dated Jul. 6, 2016, PCT Application No. PCT/CN2016/074014.

* cited by examiner

INTELLIGENT DENTAL ORNAMENT AND METHOD OF USING THE SAME

TECHNICAL FIELD

The present application relates to an intelligent dental ornament and a method of using the same.

BACKGROUND

How to noninvasively detect physiological parameters of the human body is a recent research trend. There are biochemical sensors that detect the blood glucose and/or alcohol content in the body by means of saliva, in the market. However, the biochemical sensor in the prior art is cumbersome and lacks intelligence. There is therefore a need for an apparatus for the intelligent detection of physiological parameters in saliva.

SUMMARY

In view of the above technical problems, the inventors of the present invention have creatively proposed the concept of realizing physiological parameter detection in saliva by using a dental ornament used in dental cosmetic.

Dental ornament is widely liked. However, there is not an apparatus which provides a tester in a dental ornament in the market. The present application creatively proposes an intelligent dental ornament and a method of using the same, which are used to intelligently detect physiological parameters such as blood glucose or alcohol content without affecting the aesthetics of the dental ornament, is user-friendly, and has a non-invasive detection.

In a first aspect of the present invention, there is provided an intelligent dental ornament comprising:

a dental ornament body with a cavity;

a tester located within the cavity and for detecting a physiological parameter;

a battery for providing power to the tester, the battery being located within the cavity;

the dental ornament body is provided with a through-hole for at least one pipette of the tester stretching out of the dental ornament body, and a sealing cover for sealing the through-hole;

wherein the pipette is used to acquire saliva of a subject to detect a physiological parameter by the tester.

Optionally, the intelligent dental ornament further comprises a trigger switch for triggering the tester to start test; when the trigger switch activates the tester, the sealing cover is opened, and the pipette of the tester stretches out of the intelligent dental ornament body through the through-hole to obtain the saliva of the subject; the tester detects the saliva obtained by the pipette to obtain a detection result of the physiological parameter and sends the detection result to an external device in communication with the tester; and when the trigger switch turns off the tester, the pipette of the tester retracts into the dental ornament body, and the sealing cover seals the through-hole.

Optionally, the trigger switch is connected to the tester and extends from the cavity of the dental ornament body to the outside of the dental ornament body.

Optionally, the tester comprises: a transmitter for transmitting the detection result to the external device; a controller connected to the transmitter; a biochemical sensor connected to the controller for detecting the physiological parameter in the saliva, which biochemical sensor is connected to the transmitter; and the biochemical sensor is connected to the pipette.

According to another alternative embodiment, the tester comprises a stretching device for controlling the stretching of the pipette according to the state of the trigger switch.

Optionally, the biochemical sensor comprises an alcohol test sensor and/or a blood glucose test sensor; the tester further comprises: a receiver connected to the controller for receiving an instruction of detecting the blood glucose and/or the alcohol transmitted by the external device; and the controller controls the alcohol test sensor to contact with the pipette and/or controls the blood glucose test sensor to contact with the pipette, in response to an instruction received by the receiver.

Optionally, the tester further comprises: a signal amplifier for amplifying an output signal of the biochemical sensor; the signal amplifier is located between the biochemical sensor and the transmitter, and the signal amplifier is connected to the controller and the receiver.

Optionally, the tester further comprises: a cleaning device for cleaning the at least one pipette, the cleaning device being in communication with an end of the at least one pipette remote from the biochemical sensor.

Optionally, a region of the through-hole in contact with the sealing cover is provided with a first magnetic sealing strip, and a region of the sealing cover in contact with the through-hole is provided with a second magnetic sealing strip; The first magnetic sealing strip is electrically connected with an electrode of a circuit located within the cavity, the second magnetic sealing strip is electrically connected with the other electrode of the circuit; the circuit is connected with the battery and the circuit is provided with a circuit switch, and the circuit is turned on when the circuit switch is closed in response to the triggering of the trigger switch, such that the opposite sides of the first magnetic sealing strip and the second magnetic sealing strip in the circuit are mutually exclusive to open the sealing cover.

Optionally, the stretching device comprises: a spring having one end connected to the trigger switch and the other end connected to a stretchable rod; and the stretchable rod comprising a movable rod and a fixed rod cooperating with the movable rod, the movable rod being configured to be moved by the trigger switch to close the circuit switch during moving.

Optionally, the movable rod is provided with a spherical bulge, and when the trigger switch is depressed to trigger, the spring is initially compressed to move the movable rod, the moving movable rod moving the spherical bulge to turn on the circuit switch in the circuit and in turn make the sealing cover to open, so that the pipette stretches out of the through-hole to draw the saliva of the subject.

Optionally, at least one recess is provided on the fixed rod; the movable rod is provided with at least one protrusion for engaging with at least one recess of the fixed rod, and when the protrusion is engaged with the recess, the closed state of the circuit switch is maintained.

Optionally, each pipette is provided with a curvable section; when the protrusion on the movable rod is disengaged from the recess by the large restoring force of the spring, the curvable section on each pipette is driven into a curved state so that the pipette is retracted and the circuit switch is opened, and the sealing cover seals the through-hole.

Optionally, the trigger switch is a resilient button; and/or, the pipette is a capillary that is made by memory alloy and can present a curved state partially.

Optionally, the intelligent dental ornament further comprises: a power generating device located within the cavity for charging the battery.

Optionally, the power generating device comprises: a motion structure, a generator for converting mechanical energy into electrical energy, a rectifier connected to the generator, the rectifier connecting the battery, the generator connecting the motion structure, a portion of the motion structure extending to the outside of the dental ornament body and moving with chewing of the oral cavity of the subject.

Optionally, the dental ornament further comprises a dental ornament cosmetic cover that seals the cavity of the dental ornament body.

Optionally, the trigger switch is a wireless control switch.

According to another aspect, there is proposed a method of using the above-described intelligent dental ornament, comprising:

When the triggering switch activates a tester located in the dental ornament body, the sealing cover of the intelligent dental ornament is opened and the pipette of the tester stretches out of the dental ornament body through the through-hole in the dental ornament body;

the pipette of the tester draws the saliva of the subject;

the tester detects a physiological parameter in the saliva, obtains a detection result, and sends the detection result to an external device in communication with the tester.

Optionally, before the sealing cover of the intelligent dental ornament is opened, the method further comprises: the intelligent dental ornament is communicatively connected to the external device.

Optionally, the method further comprises: when the trigger switch turns off the tester, the pipette of the tester presents a partially curved state and retracts into the dental ornament body, and the sealing cover seals the through-hole.

According to the above technical solution, in the intelligent dental ornament of the embodiment of the invention and the method of using the same, a tester for detecting a physiology parameter is installed within the dental ornament body, and when the user is ready to use, the trigger switch can be activated to start the tester, so that the test results can be quickly obtained. Thus environment and device limitations of detecting the physiological parameters such as alcohol and blood glucose in the prior art are avoided, and the physiological parameters in the saliva can be detected intelligently without affecting the aesthetics of the dental ornament. The technical solution is simple in operation, reduces pain of the user, is reusable, and saves cost.

BRIEF DESCRIPTION OF THE DRAWINGS

In order to more clearly illustrate the technical solutions of the embodiments of the present invention, the drawings which are required to be used in the description of the embodiments will be briefly introduced below. It will be apparent that the drawings described below are only some embodiments of the present invention. Other embodiments will be apparent to those skilled in the art according to the drawings without expending inventive effort. It is to be understood that the embodiments described hereinafter are for the purpose of explaining the present invention only and are not to be construed as limiting the scope of the invention. And it is to be understood that the drawings are not drawn to scale, and rather that some elements may be exaggerated to highlight the inventive aspects of the invention.

Figure 1:
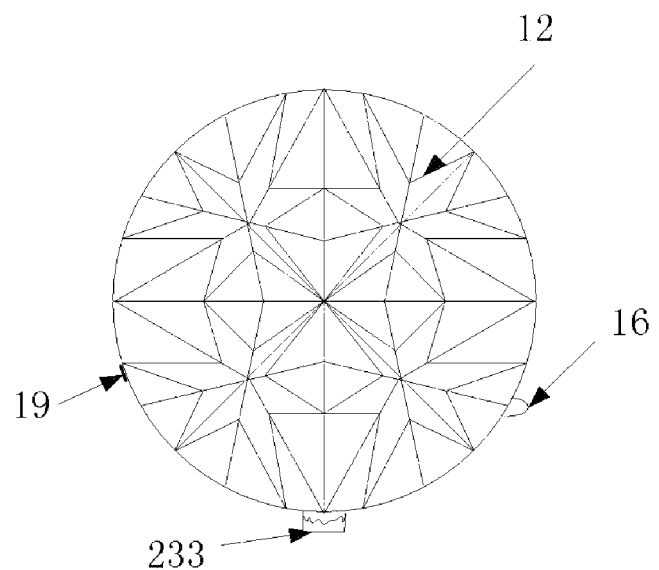
FIG. 1 is a schematic front view of an intelligent dental ornament according to an embodiment of the present invention.
Figure 2A:
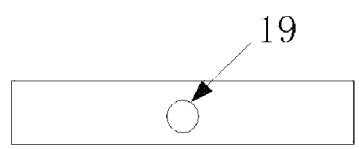
FIG. 2A is a schematic left side view of the intelligent dental ornament shown in FIG. 1.
Figure 2B:
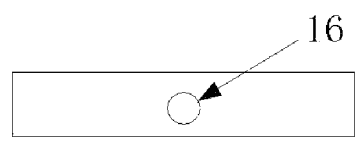
FIG. 2B is a schematic right side view of the intelligent dental ornament shown in FIG. 1.

DESCRIPTION OF REFERENCE NUMERALS dental ornament body 11, dental ornament decorative cover 12, cavity 13, tester 14, battery 15, trigger switch 16, pipette of the tester 17, through-hole in the denture body 18, sealing cover 19, cleaning device 20, first magnetic sealing stripe 21a, second magnetic sealing stripe 21b, circuit 22, circuit switch 221, power generating device 23;

transmitter/wireless transmitter 141, controller 142, biochemical sensor 143, stretching device 144, capillary 145, signal amplifier 146;

spring 1441, stretchable rod 1442, movable rod 1442b, fixed rod 1442a, protrusion 1443, spherical bulge 1444, recess 1445;

generator 231, rectifier 232, motion structure 233.

DETAILED DESCRIPTION

Hereinafter, specific implementations of the present invention will be described in further detail with reference to the accompanying drawings and embodiments. The following embodiments are intended to illustrate the present invention, but are not intended to limit the scope of the invention.

As shown in FIGS. 1 to 3B, an embodiment of the present invention provides an intelligent dental ornament comprising a dental ornament body 11 and a dental ornament decorative cover 12 (as shown in FIG. 1).

Figure 3A:
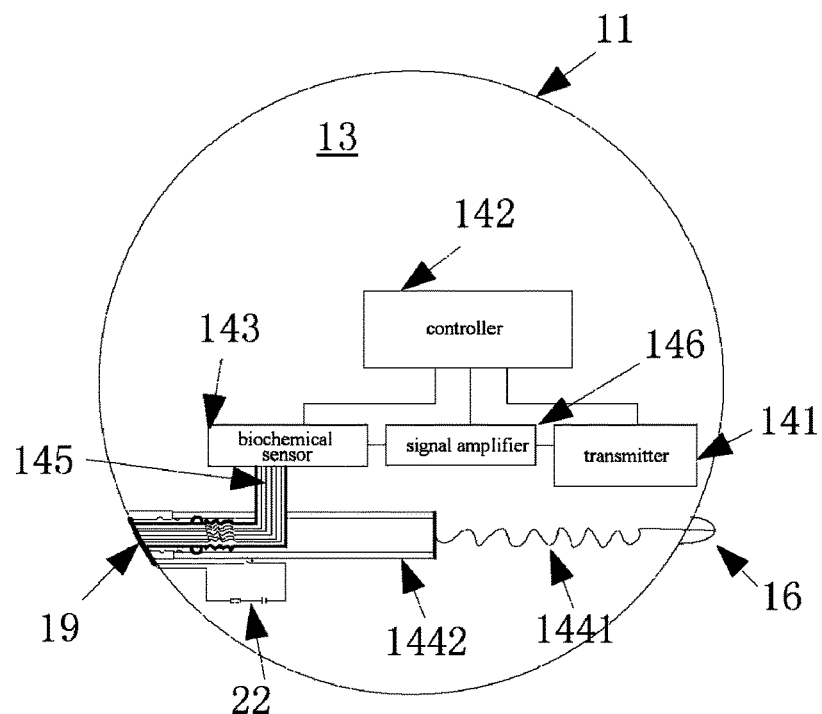
FIGS. 3A and 3B are internal structure schematic views of an intelligent dental ornament provided in accordance with an embodiment of the present invention.
Figure 3B:
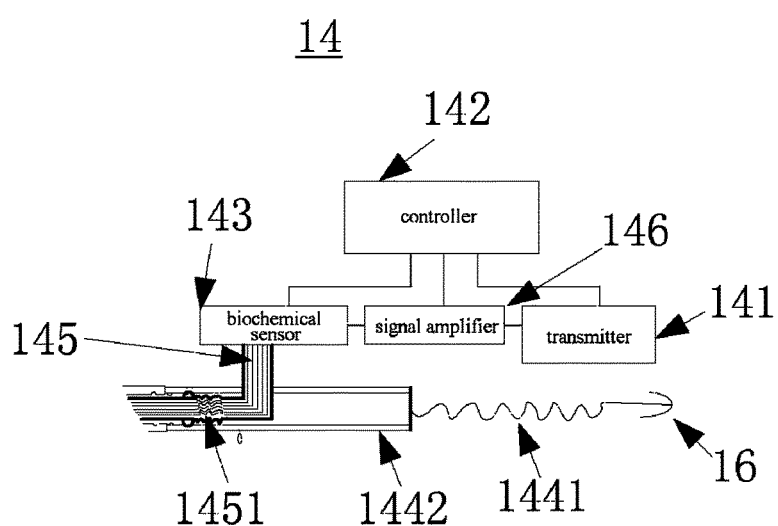

Therein, the dental ornament body 11 of the present embodiment is provided with a cavity 13 which can be sealed with a dental ornament decorative cover (as shown in FIG. 3A); the cavity is provided with a tester 14 for detecting physiological parameters, as shown in FIG. 3B.

That is to say, the tester 14 may be located within the cavity 13 of the dental ornament body 11, and a battery 15 (shown in FIG. 5) for providing operating voltage/current to the tester 14 is also provided in the cavity 13. For example, the physiological parameters that the tester 14 of the present embodiment can detect include alcohol content, blood glucose content, and the like. The alcohol content in the saliva is detected by the alcohol test sensor described below, and the blood glucose content in the saliva is detected by the blood glucose test sensor, and so on.

In addition, the tester 14 is provided with a trigger switch 16 for activating the test function or for turning off the test function, for the convenience of the user. The trigger switch 16 shown in this embodiment is connected to the tester 14 and extends from the cavity 13 of the dental ornament body 11 to the outside of the dental ornament body 11. As shown in FIG. 1, a portion located outside the dental ornament body 11 is a trigger switch 16. In other embodiments, the trigger switch 16 may also be a wireless control switch, such as an infrared sensor that cooperates with an application of an intelligent terminal, or a piezoelectric ceramic that switches on or off depending on the specific movement of the tooth. Such a trigger switch may be provided inside the cavity 13 of the dental ornament body 11. For example, the tester may be turned on/off in accordance with the instructions of the controller in the tester described below. That is, the intelligent device described below sends an instruction to the controller, and then the controller can control the trigger switch to turn on/off the tester and so on. Thus, it is possible to improve the sealing property of the intelligent dental ornament and simplify the operation of the user.

Since the trigger switch 16 shown in FIG. 1 extends from the cavity 13 of the dental ornament body 11 to the outside of the dental ornament body 11, the dental ornament body 11 may be provided with a hole-shaped region for the extending of one end of the trigger switch 16. The hole-shaped region is tightly matched with the trigger switch to ensure the sealing property of the dental ornament body 11. FIG. 1 shows a portion of the end of the trigger switch that extends out of the dental ornament body, and hole-shaped region on the dental ornament body is not shown in the Figure.

Figure 4A:
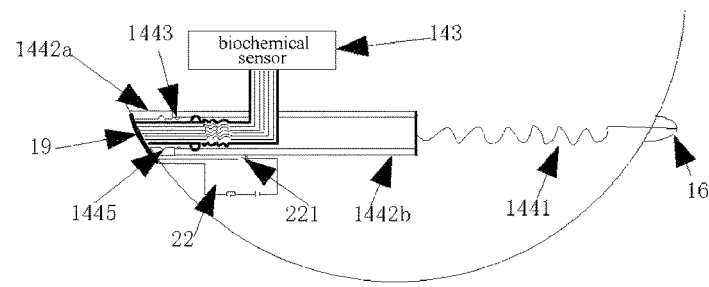
FIGS. 4A-4C are partial enlarged views of the intelligent dental ornament shown in FIG. 3A.
Figure 4B:
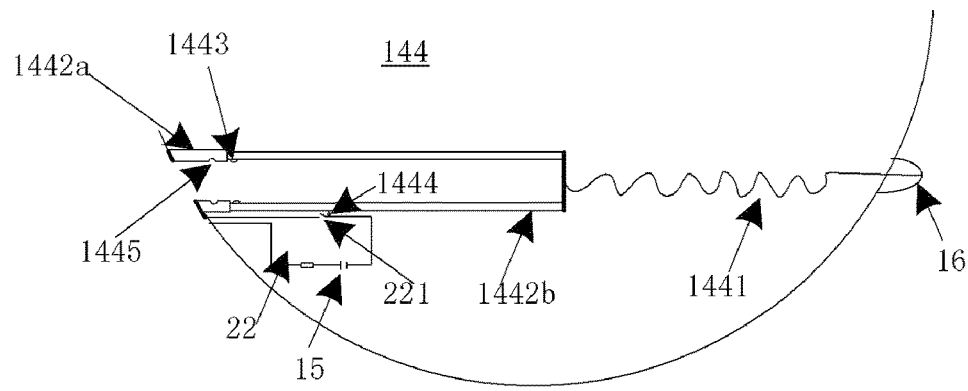
Figure 4C:
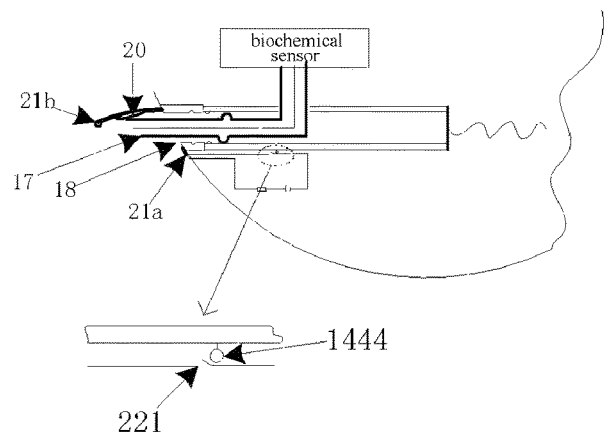

In a specific application, as shown in FIG. 4C, in order to ensure the normal operation of the tester, when the blood glucose/alcohol is to be detected by the tester, a pipette 17 included by the tester 14 for drawing the liquid to be detected needs to acquire the liquid to be detected of the user. Therefore, the dental ornament body 11 is provided with a through-hole 18 through which the pipette 17 of the tester 14 stretches out of the dental ornament body, and a sealing cover 19 for sealing the through-hole 18.

In this embodiment, in order to ensure that the dental ornament can be reused and not contaminated after each use, it is necessary to provide a sealing cover 19 for sealing the through-hole 18 so as to assure that when the tester is not used, the liquid to be detected such as saliva would not enter into the cavity of the dental ornament body 11, which effectively avoid the liquid to be detected contaminating the tester.

In specific use, the user may trigger the trigger switch 16, which extends to the outside of the dental ornament body 11, to activate the tester 14. At this time, the sealing cover 19 of the dental ornament body 11 is opened, and the pipette 17 of the tester 14 stretches out of the dental ornament body 11 through the through-hole 18 in the dental ornament body 11 to obtain the subject's saliva. The tester 14 then detects physiological parameters in the saliva according to the saliva obtained by the pipette 17, obtains a detection result, and sends the detection result to an intelligent device, such as a mobile terminal or a smart watch, which is communicatively connected to the tester. Whereby the intelligent device can display or broadcast the detection result to the user.

That is to say, in the configuration of the intelligent dental ornament of the present embodiment, the trigger switch 16 is used to start or stop the tester 14, and the controller 142 described below is used to control the biochemical sensor 143 to test the physiological parameter according to the instruction. When the trigger switch does not start the tester, the controller cannot perform the test operation even if the instruction is received.

Specifically, when the trigger switch 16 starts the tester 14, the sealing cover 19 is opened, and the pipette 17 of the tester 14 stretches out of the dental ornament body 11 through the through-hole 18 to obtain the subject's saliva.

And the tester 14 then obtains the physiological parameter of the saliva based on the saliva obtained by the pipette 17, obtains the detection result, and sends the detection result to the intelligent device communicated with the tester.

When the trigger switch 16 turns off the tester 14, the pipette 17 of the tester 14 is partially bent and retracts into the dental ornament body 11, and the sealing cover 19 seals the through-hole 18.

The intelligent dental ornament of the present embodiment can detect the physical health state of the user of the intelligent dental ornament. For example, a tester located in the cavity of the intelligent dental ornament, by detecting the physiological parameter in the user's saliva, obtains a detection result and in turn warns the user about the current physical health state. In this way, it is possible to better avoid the environment and equipment limitation in testing the physiological parameters such as alcohol and blood sugar in the prior art, and further to intelligently detect the physiological parameters in the saliva without affecting the aesthetics of the dental ornament, and the advantages such as simple operation, reduced user pain, being reusable, and cost savings can be obtained.

In order to better illustrate the structure of the tester according to an embodiment of the present invention, as shown in FIGS. 3A, 3B, 4A, 4B, 4C, and 5, the tester 14 located in the cavity 13 of the dental ornament body 11 may include an transmitter 141, a controller 142, a biochemical sensor 143, a pipette 17, and a stretching device 144.

Therein, the transmitter 141 may be a wireless transmitter for sending the test result obtained by the tester 14 to an external device (e.g., a mobile phone, an IPAD, a smart watch, etc.) communicatively connected to the tester.

The controller 142 is connected to the transmitter 141 and controls the biochemical sensor 143 to detect the physiological parameter to be detected by the biosensor 143, and when the biochemical sensor 143 acquires the detection result, the controller 142 transmits the detection result by the transmitter 141.

The biochemical sensor 143 is connected to the controller 142 for detecting the blood glucose or alcohol content in the liquid to be detected such as saliva; in addition, the biochemical sensor 143 can be connected to the transmitter 141, and then in response to the control instruction of the controller, the blood glucose or the alcohol content obtained by the biochemical sensor 143 is transmitted to the external device through the transmitter 141.

The biochemical sensor 143 is in communication with at least one pipette 17, and the biochemical sensor 143 detects physiological parameters, such as blood glucose or alcohol content, from the detected liquid drawn in the pipette 17.

In order to better realize the present invention, according to one embodiment, the pipette 17 may be a capillary 145, as shown in FIGS. 3A and 3B. The biochemical sensor communicates with a plurality of capillaries 145. Typically the number of capillaries is between 2 and 8. The capillary 145 of the present embodiment may be a capillary made of a memory alloy and capable of locally bending.

In addition, the tester according to an embodiment of the present invention further comprises a stretching device 144 for controlling the stretching of the capillary 145 in accordance with the state of the trigger switch 16, as shown in FIGS. 4A and 4B.

The biochemical sensor 143 of the present embodiment may include an alcohol test sensor and/or a blood glucose test sensor.

If the tester 14 is only a tester for detecting the blood glucose, the biochemical sensor 143 is a blood glucose test sensor; and if the tester 14 is only a tester for testing alcohol, the biochemical sensor 143 is an alcohol test sensor. The present embodiment is for the purpose of illustration only and does not limit the specific structure of the biochemical sensor.

In another possible implementation scenario, the tester 14 further comprises a receiver (not shown in the figure) connected to the controller; for example, the receiver may be a wireless receiver for receiving the instructions of testing blood sugar or testing alcohol sent by the aforementioned external device.

The controller 142 controls the alcohol test sensor to contact with the pipette 17 (e.g., the capillary 145) and/or controls the glucose test sensor to contact with the pipette 17 (e.g., the capillary 145) according to instructions received by the wireless receiver.

In addition, for ensuring the accuracy of the detect results of the tester, the tester of the present embodiment further includes a signal amplifier 146 for amplifying the signal of the biochemical sensor and transmitting it to the controller 142, the wireless transmitter 141, and/or a wireless receiver.

The signal amplifier 146 of the present embodiment is located between the biochemical sensor 143 and the transmitter 141, and the signal amplifier 146 electrically connects the controller 142 and the wireless receiver.

In addition, according to another embodiment, in order to ensure the repeated use of the intelligent dental ornament, the dental ornament is provided with a cleaning device 20 on the dental ornament body for cleaning the liquid to be detected in the capillary 145. Typically, the cleaning device 20 is in communication with one end of the capillary 145 remote from the biochemical sensor.

For example, the cleaning device 20 may be provided on a side of the sealing cover 19 facing the capillary 145, and after the sealing cover 19 seals the through-hole 18 in the dental ornament body 11, the cleaning device 20 may be in contact with the capillary 145, and further can clean the liquid to be detected in the capillary 145.

In a specific application, the cleaning device 20 may be activated carbon attached to the sealing cover 19 or other material capable of cleaning the liquid to be detected in the capillary.

Further, in order to ensure the normal operation of the tester in the case that the trigger switch is triggered, a first magnetic sealing stripe 21a is provided in the region of the through-hole 18 in contact with the sealing cover 19 in the present embodiment, and accordingly the sealing cover 19 in contact with the through-hole 18 is provided with a second magnetic seal 21b.

The first magnetic sealing stripe 21a connects one electrode (e.g., the positive electrode) of the circuit 22 located in the cavity 13, and the second magnetic sealing stripe 21b connects the other electrode (e.g., the negative electrode) of the circuit 22.

The circuit 22 of the present embodiment can be connected to the battery 15 used by the tester 14, and the circuit 22 is provided with a circuit switch 221. When the circuit switch 221 is closed, the circuit 22 is turned on, and the opposite sides of the first magnetic sealing stripe 21a and the second magnetic sealing stripe 21b in the circuit 22 are magnetized to have the same polarity so as to be mutually exclusive. At this time, the sealing cover 19 is automatically opened.

In other embodiments, the circuit 22 may also be provided with a separate battery, and does not share the battery 15 with the tester.

Of course, if the circuit switch 221 is turned off, no current flows in the circuit 22, and the opposite sides of the first magnetic sealing stripe 21a and the second magnetic sealing stripe 21b are not magnetized by the current, but are attracted to each other by the initial opposing magnetism, so that the sealing cover 19 can automatically seal the through-hole 18.

That is, after the trigger switch is first triggered, the circuit switch 221 is closed and the circuit 22 is turned on. After the trigger switch is triggered again, the circuit switch 221 is opened and the circuit 22 is opened.

As a result, it is possible to better ensure that the sealing cover seals the through-hole, and that the tester is not contaminated by the user's saliva.

In particular, the portion of the trigger switch 16 that extends outside of the body of the dental ornament body shown in FIGS. 1 to 5 may be a resilient button.

Figure 5:
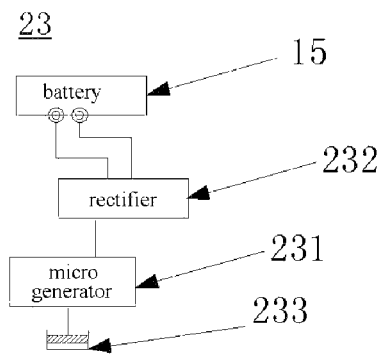
FIG. 5 is a partial schematic view of an internal structure of an intelligent dental ornament provided in accordance with an embodiment of the present invention.

In addition, the aforementioned stretching device 144 of the tester 14 may include a spring 1441 and a stretchable rod 1442; one end of the spring 1441 is connected to a trigger switch 16 (e.g., a resilient button), and the other end is connected to a stretchable rod 1442; as shown in FIG. 5, the stretchable rod 1442 includes a fixed rod 1442a and a movable rod 1442b, the fixed rod 1442a being used for cooperating with the movable rod 1442b.

In the present embodiment, the movable rod 1442b is provided with a protrusion 1443 and a spherical bulge 1444 which are located on both sides of the movable rod 1442b, respectively.

As shown in FIG. 3, the movable rod 1442b shown in FIG. 3 is a rectangular frame with an opening on the left side, and parallel long sides thereof are respectively provided with protrusions 1443, and then two protrusions 1443 protrude toward inside of the rectangular frame; a spherical bulge 1444 is located on a long side of the movable rod 1442b adjacent to the circuit 22, which spherical bulge is used to close or disconnect the circuit switch 221 of the aforementioned circuit 22.

Accordingly, the fixed rod 1442a shown in FIG. 3 is provided with a recess 1445 for engaging the protrusion 1443. When the protrusion 1443 is engaged in the recess 1445, the circuit 22 is turned on, and the capillary 145 of the tester 14 passes through the through-hole 18, and stretches out of the dental ornament body 11, thereby obtaining a liquid to be detected such as saliva.

That is, when the aforementioned trigger switch 16 (e.g., a resilient button) is first pressed (i.e., when the tester is started), the spring 1441 is initially compressed and moves the movable rod 1442b to make the protrusion 1443 in the movable rod 1442b to engages the recess 1445 of the fixing rod 1442a while urging the spherical bulge 1444 to press the circuit switch 221 in the circuit 22 to close the circuit switch 221. Then the circuit 22 is energized, and the sealing cover 19 is opened (that is, the opposite sides of the first magnetic sealing stripe and the second magnetic sealing stripe are mutually exclusive so that the sealing cover 19 is opened), and the capillary 145 stretches out of the through-hole 18 to draw the subject's saliva. It should be noted that, after the sealing cover is opened and the capillary stretches out of the through-hole, the capillary can support the sealing cover so that the sealing cover would not close automatically.

Further, movement of the movable rod 1442b drives the protrusion 1443 into engagement with the recess 1445.

The capillary of the present embodiment is a capillary made of a memory alloy and capable of collecting saliva and capable of being locally bent. When the capillary does not stretch beyond the through-hole, a portion of the capillary is in a bent state, and when the capillary stretches out of the through-hole, the capillary is entirely in a straightened state. Currently, the memory state of the capillary is a straightened state. Each capillary 145 of the present embodiment is provided with a curvable section 1451 (shown in FIG. 3B) to ensure that the capillary 145 can bend and retract into the dental ornament body 11 after it has absorbed the liquid to be detected.

When the trigger switch 16 (such as a resilient button) is pressed a second time (i.e., when the tester 14 is closed), the spring 1441 is further compressed and further moves the movable rod 1442b. At this time, since the spring 1441 is compressed to a greater extent, when the trigger switch 16 is released, the greater restoring force of the spring 1441 causes the protrusion 1443 on the movable rod 1442b to disengage from the recess 1445, and causes the curvable section of each capillary 145 to bend, i.e., such that a portion of the capillary is in a bent or compressed curved state. And the curvature of the curvable section 1451 causes the end of the to capillary 145 to move away from the through-hole 18. During this movement of the movable rod 1442b, the spherical bulge 1444 on the movable rod 1442b is moved, thereby causing the circuit switch 221 to be opened and the sealing cover 19 to seal the through-hole 18.

In the present embodiment, under the non-actuated state of the tester, the protrusion on the stretchable rod is located in front of the curvable section 1451, that is, on the side of the curvable section 1451 near the sealing cover 19.

It should be noted that the periphery of the end of the capillary of the present embodiment (the end closer to the through-hole, no including the partial capillary in the curved state described above) may be provided with a hard coating material for supporting the open state of the sealing cover after the capillary stretches out of the through-hole, to ensure that the capillary can better absorb the saliva to be detected.

In this embodiment, biochemical sensors are used to extract the blood glucose/alcohol content in the saliva and, and displaying the detection result in real time on the associated external device is realized, thereby effectively improving the test efficiency of the alcohol and/or blood glucose, while reducing the pain in the prior art test. And the intelligent dental ornament can be reused, save cost better, and does not affect the aesthetics of intelligent dental ornament, increases the practicality of intelligent dental ornament.

In addition, in order to ensure the long-term use of the intelligent dental ornament and effectively utilize the oral chewing energy when using the dental ornament, a power generating device is also provided in the intelligent dental ornament, and is located in the cavity of the intelligent dental ornament and charges the aforementioned batteries (the battery used by the circuit and the battery used by the tester).

For example, the power generating device includes a motion structure 233, a generator 231 for converting mechanical energy into electrical energy, a rectifier 232 connected to the generator, the rectifier 232 connecting the battery.

The generator 231 is connected to the motion structure 233. The motion structure 233 may be a structure manufactured by using a piezoelectric material, a portion of which is extended to the outside of the dental ornament body and moves with chewing of the subject.

The intelligent dental ornament of the present embodiment can effectively utilize the chewing energy of the user, thereby realizing the charging effect by converting the mechanical energy generated during the chewing of the human body into the electric energy used by the tester.

Figure 6:
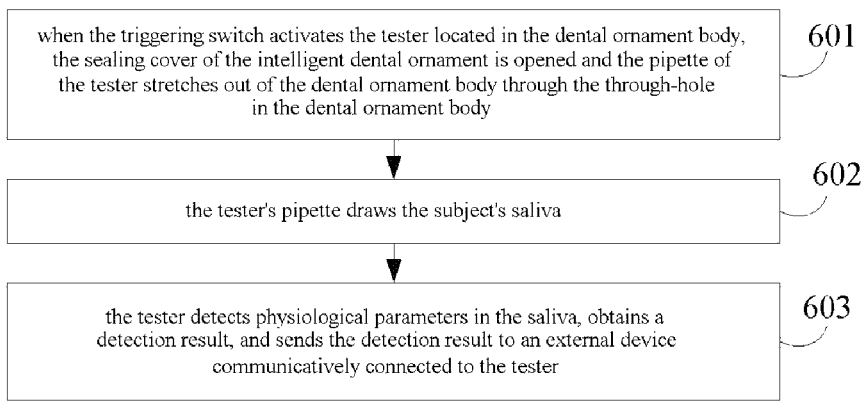
FIG. 6 is a flowchart of a method for using the intelligent dental ornament provided according to an embodiment of the present invention.

FIG. 6 shows a schematic flow diagram of a method for using the intelligent dental ornament. As shown in FIG. 6, the intelligent dental ornament of the present embodiment may be any of the intelligent dental ornaments described in any of the preceding embodiments. The method of using the intelligent dental ornament is as follows.

At 601, when the triggering switch activates the tester located in the dental ornament body, the sealing cover of the intelligent dental ornament is opened and the pipette of the tester stretches out of the dental ornament body through the through-hole in the dental ornament body;

at 602, the tester's pipette draws the subject's saliva;

at 603, the tester detects physiological parameters in the saliva, obtains a detection result, and sends the detection result to an external device communicatively connected to the tester.

Of course, when the trigger switch turns off the tester in the dental ornament body, a portion of the pipette of the tester is in a curved state, and the sealing cover of the intelligent dental ornament seals the through-hole of intelligent dental ornament. Thereby the sealing of the intelligent dental ornament is realized.

It will be appreciated that prior to step 601, the method of using the intelligent dental ornament of the present embodiment may further include a step 600 (not shown in the figure):

at 600: the tester is communicatively connected with the external device. The step enables the external device to further process the detection result, for example, to display the detection result, or to compare the detection result with a preset reference value to obtain the information of whether it is the standard is reached or whether the alarm is needed, after receiving a detection result transmitted by the transmitter of the tester.

The intelligent dental ornament of the present embodiment is simple in use and low in cost, and can be widely used. Further, the above-mentioned intelligent dental ornament can make the tester inside the intelligent dental ornament in a closed state when it is not used, and prevent the tester inside the intelligent dental ornament from being polluted.

It will be understood by those of ordinary skill in the art that the foregoing embodiments are intended to illustrate the technical solutions of the invention only and not be restrictive; while the invention has been described in detail with reference to the foregoing embodiments, it will be understood by those of ordinary skill in the art: it is possible to modify the technical solutions recited in the embodiments described above, or equivalent replace some or all of the technical features in the embodiments described above; and these modifications or replacements would not make the essence of the corresponding technical solutions to depart from the scope as defined in the claims of the present invention. It should be noted that the word "comprises" or "comprising" does not exclude presence of elements or steps that are not listed in the claims. The word "a" or "an" preceding an element does not exclude presence of a plurality of such elements. The mere fact that certain measures are recited in mutually different dependent claims does not indicate that a combination of these measures cannot be used to advantage. Any reference signs in claims should not be construed as limiting the scope.

The invention claimed is:

1. An intelligent dental ornament comprising:
a dental ornament body (11) with a cavity (13);
a tester (14) located within the cavity (13) and for detecting a physiological parameter, wherein the tester comprises at least one pipette (17);
a battery (15) for providing power to the tester (14), the battery (15) being located within the cavity (13);
the dental ornament body (11) is provided with a through-hole (18) and a sealing cover (19) for sealing the through-hole;
wherein the at least one pipette (17) is configured for stretching out of and retracting into the dental ornament body via the through-hole (18) and is used to acquire saliva of a subject to detect the physiological parameter by the tester (14).

2. The intelligent dental ornament according to claim 1, wherein
the intelligent dental ornament further comprises a trigger switch (16) for triggering the tester (14) to start test;
when the trigger switch (16) activates the tester (14), the sealing cover (19) is opened, and the pipette (17) of the tester (14) stretches out of the intelligent dental ornament body (11) through the through-hole (18) to obtain the saliva of the subject; the tester (14) detects the saliva obtained by the pipette to obtain a detection result of the physiological parameter and sends the detection result to an external device in communication with the tester; and when the trigger switch (16) turns off the tester, the pipette of the tester retracts into the dental ornament body (11), and the sealing cover (19) seals the through-hole (18).

3. The intelligent dental ornament according to claim 2, wherein the trigger switch (16) is connected to the tester (14) and extends from the cavity (13) of the dental ornament body (11) to the outside of the dental ornament body (11).

4. The intelligent dental ornament according to claim 2, wherein the tester (14) comprises:
a transmitter (141) for transmitting the detection result to the external device;
a controller (142) connected to the transmitter (141);
a biochemical sensor (143) connected to the controller (142) for detecting the physiological parameter in the saliva, which biochemical sensor (143) is connected to the transmitter (141);
and the biochemical sensor (143) is connected to the pipette (17).

5. The intelligent dental ornament according to claim 2, wherein the tester (14) comprises:
a stretching device (144) for controlling the stretching of the pipette (17) according to the state of the trigger switch (16).

6. The intelligent dental ornament according to claim 4, wherein the biochemical sensor (143) comprises: an alcohol test sensor and/or a blood glucose test sensor;
the tester (14) further comprises: a receiver connected to the controller for receiving an instruction of detecting the blood glucose and/or the alcohol transmitted by the external device;
and the controller controls the alcohol test sensor to contact with the pipette and/or controls the blood glucose test sensor to contact with the pipette, in response to an instruction received by the receiver.

7. The intelligent dental ornament according to claim 6, wherein the tester (14) further comprises: a signal amplifier (146) for amplifying an output signal of the biochemical sensor;
the signal amplifier (146) is located between the biochemical sensor (143) and the transmitter (141), and the signal amplifier (146) is connected to the controller (142) and the receiver.

8. The intelligent dental ornament according to claim 4, wherein the tester (14) further comprises: a cleaning device (20) for cleaning the at least one pipette (17), the cleaning device (20) being in communication with an end of the at least one pipette (17) remote from the biochemical sensor.

9. The intelligent dental ornament according to claim 2, wherein
a region of the through-hole (18) in contact with the sealing cover (19) is provided with a first magnetic sealing strip (21a), and a region of the sealing cover (19) in contact with the through-hole (18) is provided with a second magnetic sealing strip (21b);
the first magnetic sealing strip (21a) is electrically connected with an electrode of a circuit (22) located within the cavity (13), and the second magnetic sealing strip (21a) is electrically connected with the other electrode of the circuit (22);
the circuit (22) is connected with the battery (15) and the circuit (22) is provided with a circuit switch (221), and the circuit (22) is turned on when the circuit switch (221) is closed in response to the triggering of the trigger switch (16), such that the opposite sides of the first magnetic sealing strip (21a) and the second magnetic sealing strip (21b) in the circuit (22) are mutually exclusive to open the sealing cover (19).

10. The intelligent dental ornament according to claim 5, wherein the stretching device comprises:
a spring (1441), having one end connected to the trigger switch (1442b) and the other end connected to a stretchable rod (1442); and
the stretchable rod (1442), comprising a movable rod (1442b) and a fixed rod (1442a) cooperating with the movable rod (1442b), the movable rod (1442b) being configured to be moved by the trigger switch to close the circuit switch (221) during moving.

11. The intelligent dental ornament according to claim 10, wherein the movable rod is provided with a spherical bulge (1444), and when the trigger switch (16) is depressed to trigger, the spring (1441) is compressed to move the movable rod (1442b), the moving movable rod (1442b) moving the spherical bulge (1444) to turn on the circuit switch (221) in the circuit (22) and in turn make the sealing cover (19) to open, so that the pipette (17) stretches out of the through-hole (18) to draw the saliva of the subject.

12. The intelligent dental ornament according to claim 10, wherein at least one recess (1445) is provided on the fixed rod (1442a);
the movable rod (1442b) is provided with at least one protrusion (1443) for engaging with at least one recess (1445) of the fixed rod (1442a), and
when the protrusion (1443) is engaged with the recess (1445), the closed state of the circuit switch (221) is maintained.

13. The intelligent dental ornament according to claim 12, wherein each pipette (17) is provided with a curvable section (1451);
when the protrusion (1443) on the movable rod (1442b) is disengaged from the recess (1445) by the large restoring force of the spring, the curvable section on each pipette (17) is driven into a curved state so that the pipette (17) is retracted and the circuit switch (221) is opened, and the sealing cover (19) seals the through-hole (18).

14. The intelligent dental ornament according to claim 2, wherein the trigger switch (16) is a resilient button; and/or the pipette (17) is a capillary (145) that is made by memory alloy and can present a curved state partially.

15. The intelligent dental ornament according to claim 1, wherein the intelligent dental ornament further comprises:
a power generating device located within the cavity (13) for charging the battery (15).

16. The intelligent dental ornament according to claim 15, wherein the power generating device comprises:
a motion structure (233), a generator (231) for converting mechanical energy into electrical energy, a rectifier (232) connected to the generator, the rectifier (232) connecting the battery (15);
the generator (231) connecting the motion structure (233), a portion of the motion structure (233) extending to the outside of the dental ornament body (11) and moving with chewing of the oral cavity of the subject.

17. The intelligent dental ornament according to claim 1, wherein the dental ornament further comprises:
a dental ornament cosmetic cover (12) that seals the cavity of the dental ornament body (11).

18. The intelligent dental ornament according to claim 2, wherein the trigger switch (16) is a wireless control switch.

19. A method of using the intelligent dental ornament according to claim 1, comprising:
when a triggering switch activates a tester located in the dental ornament body, the sealing cover of the intelligent dental ornament is opened and the pipette of the tester stretches out of the dental ornament body through the through-hole in the dental ornament body;
the pipette of the tester draws the saliva of the subject;
the tester detects a physiological parameter in the saliva, obtains a detection result, and sends the detection result to an external device in communication with the tester.

20. The method according to claim 19, wherein before the sealing cover of the intelligent dental ornament is opened, the method further comprises: the intelligent dental ornament is communicatively connected to the external device.

* * * * *